United States Patent
Liu et al.

(10) Patent No.: US 8,840,768 B2
(45) Date of Patent: Sep. 23, 2014

(54) PREPARATION METHOD FOR MOLECULAR RECOGNITION SENSOR BY ELECTRODEPOSITION

(75) Inventors: Xiaoya Liu, Jiangsu (CN); Yiqun Yang, Jiangsu (CN); Chenglin Yi, Jiangsu (CN); Jing Luo, Jiangsu (CN); Haiqiang Wu, Jiangsu (CN); Sisi Jiang, Jiangsu (CN); Baoqing Wang, Jiangsu (CN); Jinqiang Jiang, Jiangsu (CN); Ren Liu, Jiangsu (CN); Shengwen Zhang, Jiangsu (CN); Jing Xu, Jiangsu (CN)

(73) Assignee: Jiangnan University, Wuxi, Jiangsu (CN)

( * ) Notice: Subject to any disclaimer, the term of this patent is extended or adjusted under 35 U.S.C. 154(b) by 157 days.

(21) Appl. No.: 13/562,410

(22) Filed: Jul. 31, 2012

(65) Prior Publication Data

US 2012/0285833 A1  Nov. 15, 2012

Related U.S. Application Data

(63) Continuation-in-part of application No. PCT/CN2010/079331, filed on Jan. 12, 2010.

(51) Int. Cl.
*C25D 13/00* (2006.01)
*G01N 33/543* (2006.01)
*G01N 27/327* (2006.01)

(52) U.S. Cl.
CPC ........ *G01N 33/5438* (2013.01); *G01N 27/3275* (2013.01)
USPC .......... 204/507; 204/403.01; 205/50; 205/91; 205/188; 205/777.5

(58) Field of Classification Search
CPC ........................ G01N 33/5438; G01N 27/3275
USPC ................. 204/507, 403.01; 205/50, 91, 188, 205/777.5
See application file for complete search history.

(56) References Cited

U.S. PATENT DOCUMENTS

2004/0126814 A1  7/2004 Singh et al.
2010/0075432 A1*  3/2010 Piletsky et al. ............... 436/131

FOREIGN PATENT DOCUMENTS

| CN | 1583804 A | 2/2005 |
| CN | 101324541 A | 12/2008 |
| CN | 101776635 A | 7/2010 |
| WO | WO 2007095181 A2 | 8/2007 |
| WO | WO 2008107651 A1 | 9/2008 |

OTHER PUBLICATIONS

Fang et al "Electrochemical sensor based on molecular imprinting by photo-sensitive polymers", Biosensors and Bioelectronics, 24 (2009) 3164-3169.*
Ngounou et al "Parallel synthesis of anodic and cathodic functionalized electrodeposition paints as immobilization matrix for amperometric biosensors", Biochemistry, 71 (2007) 81-90.*

* cited by examiner

*Primary Examiner* — Xiuyu Tai
(74) *Attorney, Agent, or Firm* — George G. Wang; Bei & Ocean

(57) ABSTRACT

A preparation method for molecular recognition sensor by electrodeposition is provided. The preparation method is as following: forming molecularly imprinted polymeric micelles by self-assembly of ionic type photosensitive copolymers; forming a film on the surface of an electrode by electrodepositing the molecularly imprinted polymeric micelles at a constant potential; crosslinking the electrodeposited micellar film via ultraviolet light irradiation; extracting the template molecules from the crosslinked film to obtain electrode modified by the molecularly imprinted polymeric micellar film; and connecting the modified electrode with a sensor device and a computer to construct a molecular recognition sensing system capable of specifically detecting the template molecules.

20 Claims, No Drawings

PREPARATION METHOD FOR MOLECULAR RECOGNITION SENSOR BY ELECTRODEPOSITION

CROSS-REFERENCE TO RELATED APPLICATION

This is a continuation-in-part (CIP) application, claiming benefit from PCT Application No. PCT/CN2010/079331 file Jan. 12, 2010, the content of which is incorporated herewith in its entirety by reference.

FILED OF THE INVENTION

The invention relates to a preparation method for molecular recognition sensor by electrodeposition, including: design and synthesis of ionic type photosensitive copolymers, preparation of molecularly imprinted polymeric micelles entrapping template molecules via the self-assembly of the copolymers, fabrication of the modified electrode by direct electrodepositing the imprinted polymeric micelles on the surface of electrode and subsequent extracting the template molecules. The modified electrode could be used as molecular recognition sensors, a subject matter within a combinational technical field of polymer materials and biomimetic sensors.

BACKGROUND OF THE INVENTION

Molecular recognition defines a process of the selective bonding between a receptor (host) and a substrate (guest) to generate a particular function. The concept of molecular recognition originates from the research of interaction relationships between the hosts and guests in the process of life, such as enzyme and substrate, the proteins and nucleic acids, hormones and receptors, antigen and antibody. With the advance of the life science and technology, many enzymes and antibodies extracted from the organism have been used for biological sensing and the resultant biosensors have been applied in the field of clinical testing, pharmaceutical analysis, gene diagnosis, cancer treatment and environmental monitoring. However, there are several significant disadvantages of these biosensors, such as stringent environmental requirements, short shelf life and high production cost. Recently, the molecularly imprinted technology (MIT), developed from the perspective of bionics, combining the advantages of polymer materials science, analytical chemistry, life sciences and bioengineering, artificially synthesize polymer materials which could exactly match with a particular molecule (imprinted molecules, template molecules) in space and binding sites to realize molecular recognition. The obtained molecularly imprinted polymers (MIPs), so-called "plastic antibodies", possess more practical value because of the similar recognition properties and selectivity as natural antibodies, as well as the same high stability and environmental tolerance as polymers.

During the procedure of fabricating molecular recognition sensors with the molecular imprinted polymers, the immobilization of imprinted polymers onto the surface of transducer is the key point. Although polymeric film could be formed on the surface of transducer through traditional coating methods, there are several disadvantages of those obtained manual coatings, such as inhomogeneity, uncontrollable coating thickness, and easy desquamation from the surface of transducer. Due to those drawbacks, the molecular recognition sensors prepared by the coating methods have inferior reproducibility and stability, as well as short shelf-life. With the development of polymer synthesis technology, in-situ grafting methods are applied to immobilize imprinted copolymer onto the surface of transducer. A stable covalent binding could be formed between the transducer and the imprinted polymers via this method. The resultant imprinted polymer film is a nanometer ultra-thin film of uniform thickness, possessing good molecular recognition sensing property. However, the controlled radical polymerization reaction (such as ATRP, RAFT) used in the in-situ grafting method needs complex catalytic initiator system and harsh reaction conditions, which greatly retard the wide application of this method. Electrodeposition provides another efficient way to form a film on transducer. Compared with the aforementioned methods, the film formed by electrodeposition is uniform and controllable in thickness. In addition, the electrodeposited films possess excellent adhesion and good weather ability. Currently, the electrodeposition technology, so-called "electrophoresis" in the industry, has been widely used in the coating of the cars and various kinds of metal devices.

SUMMARY OF THE INVENTION

The invention aims to provide a simple and controllable preparation method to construct molecular recognition sensor by electrodeposition. The preparation method of this invention involves the formation of ionic type photosensitive molecularly imprinted micelles by self-assembling and then electrodepositing the imprinted micelles on the surface of the electrode to form a molecular recognition polymeric film. The whole process is simple, controllable, and of low cost, which can overcome the drawbacks of the existing preparation technologies for molecular recognition sensors.

Another purpose of the present invention is to broaden the range of target molecules that could be recognized. Through trapping different template molecules into the self-assembled polymeric micelles, one ionic type photosensitive copolymer could recognize a variety of molecules. In addition, by designing different types of the ionic type photosensitive copolymer and changing the micellar concentration or the deposition conditions, the properties of the molecularly imprinted films can be controlled and the relationship between the structure of the polymers and the performance of the constructed molecular recognition sensors can be finally established.

Technical Scheme

A preparation method for molecular recognition sensor by electrodeposition: forming molecularly imprinted polymeric micelles encapsulating template molecules by self-assembly of the ionic type photosensitive copolymers; forming a film on the surface of an electrode by electrodepositing the molecularly imprinted polymeric micelles at a constant potential; crosslinking the electrodeposited micelles via ultraviolet light irradiation; extracting the template molecules from the crosslinked film to obtain electrode modified by the molecularly imprinted polymeric micellar film; and connecting the modified electrode with a sensor device and a computer to assemble a molecular recognition sensing system capable of specifically detecting the template molecules. Details are as following:

1. The preparation of the ionic type photosensitive copolymers:

1.1 The ionic type photosensitive copolymers were synthesized by copolymerization of photosensitive monomer, ionic monomer and hydrophobic monomer:

The photosensitive monomer was selected from:

7-(4-vinylbenzyloxy)-4-methylcoumarin, 2-cinnamic acyloxyethyl methylacrylate or 4-methyl-[7-(methacryloyl)oxy]ethyl]oxy]coumarin.

The ionic monomer was selected from:

4-vinylbenzene sulfonic acid, 2-(methacryloyl)oxyethyltrimethylammonium chloride, 2-acrylamide-2-methylpropanesulfonic acid, acrylic acid, methacrylic acid, 4-vinylbenzoic acid, 4-vinyl pyridine, 2-vinyl pyridine, melic anhydride, acrylic-2-(dimethylamino)ethyl ester, methyl methacrylate-2-(dimethylamino)ethyl ester, diethylamineethyl methylacrylic acid ester or 2,4-diamino-6-vinyl-S-triazine vinyldiaminotriazine.

The hydrophobic monomer was selected from:

hydroxyethyl acrylate, hydroxyethyl methacrylate, hydroxypropyl methacrylate, hydroxypropyl acrylate, acrylic poly(ethylene glycol) ester, methylacrylic poly(ethylene glycol) ester, styrene, acrylic ester, methacrylic acid ester.

The ionic type photosensitive copolymer was synthesized using the different types of monomers as-described above through various polymerization methods, such as normal free radical solution polymerization, free radical dispersion polymerization, free radical emulsion polymerization or free radical precipitation polymerization.

1.2 The ionic type photosensitive copolymers were synthesized by grafting the existing normal ionic type copolymers with photosensitive monomer.

The ionic type copolymer was selected from: ionic polyurethane, ionic epoxide resins, ionic acrylate resins;

The photosensitive monomer was selected from: (hydroxyethyl)acrylate, (hydroxyethyl)methacrylate, acrylamide, methylacrylamide.

1.3 The ionic type photosensitive copolymers were obtained through synthesizing polyaniline using reactive polymers with photosensitive moieties as dispersant, and then ionizing the synthetic polyaniline to get positive charge by modification with acid.

The reactive polymers used as dispersant were synthesized with photosensitive monomers and hydrophilic monomers;

The hydrophilic monomer was selected from: acrylamide, amino styrene;

The photosensitive monomer was selected from:

7-(4-vinylbenzyloxy)-4-methylcoumarin, 2-cinnamic acyloxyethyl methylacrylate or 4-methyl-[7-(methacryloyl)oxy]ethyl]oxy]coumarin.

All the ionic type photosensitive copolymers used in the present invention could be provided by School of Chemical and Material Engineering in Jiangnan University.

2. Preparation of the solution of the ionic type photosensitive copolymer: Certain amount of ionic type photosensitive copolymers were dissolved in good solvent to get a solution with a solid content of 0.5%~60%. Good solvent was one solvent or two mixed solvents selected from: dimethylformamide (DMF), dimethyl sulfoxide (DMSO), tetrahydrofuran (THF), acetone, isopropyl alcohol, butanol, methanol, 2-butoxyethanol, acetonitrile. Then, the pH levels of the copolymer solution was controlled among 2~5 or 8~12 by adding acid or alkali solutions. The acid was selected from: hydrochloric acid, acetic acid, formic acid, lactic acid, propionic acid, butyrate, sulfuric acid, methane sulfonic acid, or hydroxyl propane sulfonic acid; while the alkali was selected from: sodium hydroxide, potassium hydroxide, triethylamine, iminobisethanol, triethanolamine or ammonia.

3. The preparation of the ionic type photosensitive micelles entrapping the template molecules by self-assembly approach: The template molecules were added to the copolymer solution prepared in the Step 2 (the mass percent of the template molecules to the ionic type photosensitive copolymer is 2%~30%), and completely dissolved and complexed with the ionic type photosensitive copolymer under stirring; Then ultrapure water as poor-solvent was added dropwise into the polymer solution under stirring, until the volume of solution is 1.5~4 fold than the initial volume, which induces the microphase separation and self-assembling of the ionic photosensitive copolymer to form the ionic type photosensitive molecularly imprinted micelles with the template molecules entrapped in; This solution was kept stirring for 5~12 hours to ensure the complete self-assembly of ionic type photosensitive copolymers thoroughly; Subsequently, the molecularly imprinted micelles solution was added dropwise into 5 times volume of ultrapure water to "quench" the micelles, followed by 3~5 hours' stirring and then dialysis or evaporation to remove good solvent to obtain a 0.1~30 wt % ionic type photosensitive molecularly imprinted micelles aqueous solution.

4. Electrodepositing ionic type photosensitive molecularly imprinted micelles to form film on transducer: The electrode was cleaned with a fresh "Piranha" solution (a 1:3 mixture of 30% $H_2O_2$ and conc. sulfuric acid), then rinsed with ultrapure water and alcohol; the pretreated electrode was immersed into the ionic type photosensitive molecularly imprinted micelles solution and then applied with a constant potential to electrodeposit the micelles onto the surface of electrode and form film; the obtained electrode after the electrodeposition was subjected to UV irradiation to lock the structure of the micellar film.

5. Extraction of the templates: The obtained electrode in step 4 was immersed in polar solvent under stirring for 1~36 hours to extract the template molecules, and then rinsed with ultrapure water to get the electrode modified with the ionic type photosensitive molecularly imprinted micelles electrodeposited film; The polar solvent was one solvent or two mixed solvents selected from: water, acetic acid, ethanol, methanol, acetonitrile, N,N-dimethylformamide, dimethyl sulfoxide, or ethyl acetate, with the volume ratio of components in the mixed solvent of 1:1~1:9 (v/v).

6. Fabrication of the molecular recognition sensor: The electrode modified with the molecularly imprinted film prepared in step 5 was connected with a sensor device to construct a molecular recognition sensor.

The template molecules mentioned above were common molecules selected from the field of food safety testing, bio-pharmaceuticals or environmental monitoring. Templates for food safety testing: antibiotic, hormone, tonyred, melamine, methanal, mintacol, thiophos, nicotine, morphine or caffeine; Templates for bio-pharmaceuticals: glucose, adrenaline, dopamine, ascorbic acid, purine, pyrimidine, DNA, protein or amino acid; Templates for environmental monitoring: trinitrotoluene (TNT), formaldehyde, paraquat or vomitoxin.

The described electrode is the electrode of sensing device, and the surface of electrode is a material with electrical conductivity, such as gold, platinum, glassy carbon, stainless steel, tinplate or ITO conductive glass.

The obtained sensors collect molecular signals and transfer these signals into electrical signals, quality signals, substrate vibration frequency signals or spectrum signals that could be recognized by computer.

In the as-described ionic type photosensitive molecularly imprinted micelles, the interactions between the template molecules and the ionic type photosensitive copolymers could be one or several types of the interactions including hydrogen bonding, electrostatic interaction, and coordination.

During the described electrodeposition process, the ionic photosensitive molecularly imprinted micelles aqueous solution can be mixed with conducting materials to improve the performance of the formed micellar film. The conducting materials were prepared by the modification of carbon nanotube, graphene, gold nanoparticles, and silver nanoparticles with amphiphilic copolymers or surfactants.

During the electrodeposition of the micelles, the applied constant potential is contrary to the charge of the molecularly imprinted micelles, with applied potential of −30 V~+30 V and the deposition time of 5 s~10 min.

Changing the concentration of the ionic type photosensitive molecularly imprinted micelles or electrodeposition conditions can adjust the thickness and density of the imprinted film on the electrode surface, and finally control the detection range and sensitivity of the fabricated molecular recognition sensor.

The applications of the molecular recognition sensors: The recognizable molecules by the fabricated sensors are the template molecules (imprinted molecules) used in the self-assembly process, resulting in the good selectivity of the obtained sensors. To use it, the molecular recognition sensor should be connected with the computer and the electrode should be contacted with the text solution containing the template molecules.

The ionic type photosensitive copolymers were synthesized with different types of monomers via copolymerization methods, including normal free radical solution polymerization, free radical dispersion polymerization, free radical emulsion polymerization or free radical precipitation polymerization. All the ionic type photosensitive copolymers synthesized and used in the present invention could be provided by School of Chemical and Material Engineering in Jiangnan University.

Beneficial Effects

The beneficial effects of the present invention: the present invention overcomes the deficiencies of the existing molecular recognition sensors in the preparation methods, stability, sensitivity and reproducibility. The free radical polymerization of preparing the ionic type photosensitive copolymers and the electrodeposition technology of immobilizing imprinted polymers onto the surface of transducer utilized in our invention are efficient, easy to carry out and has already been industrialized. In addition, the obtained electrode sensor not only shows good molecular recognition ability, but also excellent sensitivity and reversibility, possessing better stability and practicability than conventional molecular recognition sensors. Meanwhile, the selectivity of the sensor toward analytes is tailorable and adjustable by means of choosing different template molecules and designing the appropriate copolymers structure. Hence, the present invention could be widely used in the fields of chemical industry, biomedicine, food industry, environmental protection and so on.

DETAILED DESCRIPTION OF PARTICULAR EMBODIMENTS OF THE INVENTION

The present invention is further illustrated but not limited by the following examples.

Example 1

(1) Preparation of Ionic Photosensitive Copolymer

Synthesis of ionic photosensitive copolymer (4-vinyl pyridine-co-acrylic acid-co-(2-hydroxymethyl-(4-methyl coumarin)oxyethyl-methyl acrylate)), abbreviated as P(4VP-co-AA-co-CGMA). 0.525 g (0.005 mol) 4-vinylpyridine, 0.36 g (0.005 mol) acrylic acid, 3.18 g (0.01 mol) 2-hydroxymethyl-(4-methyl coumarin) ethyl-methyl acrylate, and 0.049 g (0.3 mmol, 1.5% of the total molar weight of monomers) azodiisobutyronitrile as initiator were dissolved in 25 mL dioxane. The mixture was degassed with nitrogen gas for 20 min and sealed under vacuum, then placed in a preheated oil bath (70° C.) for 12 hours under stirring. The resultant polymers were purified by reprecipitation three times into mixed solvents of methanol and water (8:2 in volume ratio) and then dried under vacuum at 30° C.

(2) Preparation of Molecularly Imprinted Polymeric Micelles

The obtained copolymers were dissolved in dimethyl sulfoxide to get solution with a solid content of 20 wt %. The prepared solution was acidified with acetic acid and glucose was added with as the template molecule (the mass ratio of glucose/copolymer is 1/2). Ultrapure water was added dropwise into the above solution under stirring until the concentration of the polymer solution reached 4% by weight. The molecularly imprinted polymeric micelles solution was obtained after removing DMSO by dialysis and adjusting the pH level to 6 by acetic acid.

(3) Preparation of molecular recognition electrochemical sensor: The electrode was treated with "Piranha" solution, rinsed with ultrapure water and ethanol under sonication and dried. The pretreated electrode was immersed into the molecularly imprinted polymeric micelles solution and applied with a −10 V potential to make the imprinted micelles with positive charge move and deposit onto the electrode surface. The electrode after electrodeposition was rinsed with a lot of ultrapure water, and then subjected to UV irradiation at a wavelength of 365 nm to photo-cross-link the micellar film on the electrode. The electrode was soaked in ethyl acetate solution under stirring for 6 hours to get the target electrode modified with molecularly imprinted micelles electrodeposited film (namely "MIP electrode") by the extraction of glucose. The MIP electrode was connected with electrochemical workstation to form the molecular recognition sensor. The obtained MIP sensor possesses good selectivity for glucose, with the detection limit of $5 \times 10^{-7}$ mol/L and the linear response range from $2 \times 10^{-5} \sim 6.8 \times 10^{-3}$ mol/L. The sensor shows small response to the maltose, xylose and isomers galactose with different molecular size and shape, indicated by the ratios of peak current to glucose were 0.13, 0.15, and 0.22, respectively.

Example 2

(1) Preparation of the Ionic Photosensitive Copolymer

Synthesis of poly(maleic anhydride-co-styrene-co-(7-(4-vinyl benzyloxy)-4-methylcoumarin), abbreviated as P(Man-co-St-co-VM). 2.352 g (0.024 mol) maleic anhydride, 1.56 g (0.015 mol) styrene, 1.46 g (0.005 mol) 7-(4-vinyl benzyloxy)-4-methylcoumarin, and the initiator 0.072 g (0.44 mmol) azodiisobutyronitrile were dissolved in 25 mL dioxane and added into flask. The mixture was degassed with nitrogen gas for 50 min and sealed under vacuum, then placed in a preheated oil bath (65° C.) for 8 hours under stirring. The resultant polymers were purified by reprecipitation three times into mixed solvents of methanol and water (8:2 in volume ratio) and then dried under vacuum at 30° C. The resultant polymer was dissolved in DMF and then added dropwise with alkaline aqueous solution. The resultant solution was heated to 90° C. to hydrolyze the maleic anhydride. The ionic photosensitive copolymers were obtained after dialysis and freeze-drying.

(2) Preparation of Molecularly Imprinted Polymeric Micelles

The obtained copolymers were dissolved in dimethyl sulfoxide to get solution with a solid content of 10 wt %. The prepared solution was alkalized with NaOH solution and glucose was added as the template molecule (the mass ratio of glucose/copolymer is 3/10). Ultrapure water was added dropwise into the above solution under stirring until the concentration of the polymer solution lowered to 2 wt %. The molecularly imprinted polymeric micelles solution was obtained after dialysis, with the pH controlled to be 8~10.

(3) Preparation of molecular recognition electrochemical sensor: the fabrication procedure of the sensor was similar to Example 1, except that the applied potential in this case was +1 V. The prepared sensor possesses good selectivity for glucose, with the detection limit of $5 \times 10^{-8}$ mol/L and the linear response range of $4 \times 10^{-7} \sim 9 \times 10^{-5}$ mol/L. There is a large shift of the redox peaks of the glucose's analogues detected by the glucose sensor from −0.51 V overlapped with the peak of glucose to −0.38 V, resulting in excellent selectivity of the glucose sensor without the disturbance of analogues of the glucose.

Example 3

(1) Preparation of Ionic Photosensitive Copolymer

Synthesis of amphiphilic poly((2,4-diamino-6-vinyl-S-triazine)-co-methylacrylic poly(ethylene glycol) ester-co-(2-cinnamic acyloxyethyl methylacrylate)), abbreviated as P(VDAT-co-MPEG-co-CEMA). 2.74 g (0.02 mol) 2,4-diamino-6-vinyl-S-triazine, 4.75 g (0.01 mol) methylacrylic poly(ethylene glycol) ester, 2.46 g (0.01 mol) 2-cinnamic acyloxyethyl methylacrylate, and the initiator 0.099 g azodiisobutyronitrile were dissolved into 25 mL dioxane and added into flask. The mixture was degassed with nitrogen gas for 50 min and sealed under vacuum, then placed in a preheated oil bath (65° C.) for 8 hours under stirring. The resultant polymers were purified by reprecipitation three times into mixed solvents of methanol and water (1:1 in volume ratio) and then dried under vacuum at 30° C.

(2) Preparation of Molecularly Imprinted Polymeric Micelles

The obtained polymers were dissolved in DMF and uracil was then added as the template molecule (3 times the amount of the monomer triazine). Ultrapure water was added into the above solution at a rate of 7 μL/min under stirring until the water volume content was 50% at room temperature. With the solution stirred overnight, the imprinted micelles were quenched via adding polymer solution into a large amount of water, following with 5 hours' stirring. The molecularly imprinted polymeric micelles solution was obtained after dialysis for 3 days to remove DMF, and the pH of solution was adjusted to 4 by HCl solution.

(3) Preparation of Molecular Recognition Sensor Based on Electrochemical Quartz Crystal Microbalance (EQCM)

The EQCM electrode was rinsed with ultrapure water and ethanol under sonication and dried by $N_2$ gas. The EQCM electrode was immersed into the 40 mL imprinted polymeric micelles solution (the concentration was 10 mg/mL), applied with a potential of −0.8 V for 10 min, and then subjected to UV irradiation. The obtained electrode was soaked in water to extract uracil. Finally, the prepared electrode modified with imprinted self-assembled micelles film was connected with EQCM, which could detect the uracil in solution with the detection limit of $7.2 \times 10^{-8}$ mol/L. Even with the disturbance of thymine, guanine, adenine, and cytosine in a concentration of one or three times the amount of triazine, the detection limit of the sensor could still be maintained at $6.4 \times 10^{-7}$ mol/L, and the linear response range was $8 \times 10^{-7} \sim 2 \times 10^{-5}$ mol/L.

Example 4

(1) Preparation of Ionic Photosensitive Copolymer

Synthesis of poly(acrylic-2-(dimethylamino)ethyl ester)-co-acrylic acid-co-(2-cinnamic acyloxyethyl methylacrylate)), abbreviated as P(DM-co-AA-co-CEMA), through normal free radical solution polymerization. 4.29 g (0.03 mol) acrylic-2-(dimethylamino)ethyl ester, 5.04 g (0.007 mol) acrylic acid, 2.46 g (0.01 mol) 2-cinnamic acyloxyethyl methylacrylate, and the initiator 0.164 g (0.1 mmol, 1.0% of the total molar weight of monomers) azodiisobutyronitrile were dissolved in 25 mL dioxane and added into flask. The mixture was degassed with nitrogen gas for 30 min and sealed under vacuum, then placed in a preheated oil bath (70° C.) for 12 hours under stirring. The resultant polymers were purified by reprecipitation three times into acetone and then dried under vacuum at 30° C.

(2) Preparation of Molecularly Imprinted Polymeric Micelles

The obtained ionic photosensitive copolymer prepared was dissolved in ultrapure water and bovine serum albumin was then added as the template molecule (10% of the total molar weight of acrylic acid units in polymer). The imprinted micelles entrapping bovine serum albumin were obtained after the complete complexation between polymers and templates under stirring, and the pH of solution was adjusted to 4~5 by HCl solution.

(3) Preparation of Molecular Recognition Sensor Based on Electrochemical Quartz Crystal Microbalance (EQCM)

The EQCM electrode was rinsed with ultrapure water and ethanol under sonication and dried by N2 gas. The EQCM electrode was immersed into the 40 mL imprinted polymeric micelles solution (the concentration was 30 mg/mL), applied with a potential of −1.0 V for 30 s, and then subjected to UV irradiation for 10 min. The obtained electrode was soaked in acetate buffer solution to extract bovine serum albumin. Finally, the prepared electrode modified with imprinted self-assembled micelles film was connected with EQCM, and then detected the bovine serum albumin in solution. The detection limit of the sensor was 3.7 μg/L and the linear response range was from 5.2 to 120 μg/L. The presence of ascorbic acid, glucose, adrenaline and dopamine in physiological concentrations has no interference of the sensor.

Example 5

(1) Preparation of Ionic Photosensitive Copolymer

Isocyanato-terminated ionic polyurethane was dissolved into anhydrous methyl ethyl ketone, and then added with hydroxyethyl acrylate (the molar ratio of the polyurethane to hydroxyethyl acrylate is 1:2). The mixture was reacted in oil bath at 60° C. until the isocyano groups disappeared. The resultant cation type photosensitive polymers were purified by reprecipitation three times into petroleum ether and then dried under vacuum at 30° C.

(2) Preparation of Molecularly Imprinted Polymeric Micelles

The obtained cation type photosensitive polymers were dissolved in DMSO to get a solution with solid content of 20%. The polymer solution was acidified with acetic acid and mintacol was added as the template molecule. Ultrapure water was added dropwise into the above solution under stirring until the solid content of the solution lowered to 4 wt %. The molecularly imprinted polymeric micelles solution was obtained after removing DMSO by dialysis and adjusting the pH level to 6 by acetic acid.

(3) Preparation of molecular recognition electrochemical sensor: The electrode was treated with "Piranha" solution, rinsed with ultrapure water and ethanol under sonication and dried. The pretreated gold electrode was immersed into the molecularly imprinted polymeric micelles solution and applied with a −10 V potential to make the imprinted micelles with positive charge move and deposit onto the electrode surface. The electrode after electrodeposition was rinsed with a lot of ultrapure water, and then subjected to UV irradiation at a wavelength of 300 nm to photo-cross-link the micellar film on the electrode. The electrode was subsequently soaked in ethyl acetate solution under stirring for 6 hours to extract the mintacol and obtain the target electrode modified with molecularly imprinted micelles electrodeposited film (namely "MIP electrode"). The MIP electrode was connected with electrochemical workstation to form the molecular recognition sensor. The obtained MIP sensor possesses good selectivity for mintacol, with the detection limit of $5 \times 10^{-7}$ mol/L and the linear response range from $1 \times 10^{-4} \sim 8.0 \times 10^{-7}$ mol/L. The sensor shows negligible response to the analogues of mintacol, phoxim, and nitrobenzene.

Example 6

(1) Preparation of Ionic Photosensitive Copolymer 2.45 g acrylamide, 0.62 g 7-(4-vinylbenzyloxy)-4-methyl-coumarin, and the initiator 0.072 g azodiisobutyronitrile were dissolved in 25 mL dioxane. The mixture was degassed with nitrogen gas for 50 min and sealed under vacuum, then placed in a preheated oil bath (65° C.) for 24 hours under stirring. The polymers were purified via precipitation in dichloromethane. The purified polymer was dissolved into hot HCl solution and then cooled to 0° C. Subsequently, hydrochloric acid solution containing 0.5 g aniline and 1.3 g aqueous solution of ammonium persulfate were added to the polymer solution. After 8 hours under stirring, the ionic photosensitive polymer was centrifugated and purified from the obtained polyaniline dispersing solution.

(2) Preparation of Molecularly Imprinted Polymeric Micelles

The synthetic ionic photosensitive polymers were dissolved in DMSO to get a solution with solid content of 20%. The polymer solution was acidified with lactic acid and TNT was added as the template molecule. Ultrapure water was added dropwise into the above solution under stirring until the solid content of the solution lowered to 4 wt %. The molecularly imprinted polymeric micelles solution was obtained after dialysis with the pH level adjusted to 6 by acetic acid.

(3) Preparation of molecular recognition electrochemical sensor: The electrode was treated with "Piranha" solution, rinsed with ultrapure water and ethanol under sonication and dried. The pretreated gold electrode was immersed into the molecularly imprinted polymeric micelles solution and applied with a −25 V potential to make the imprinted micelles with positive charge move and deposit onto the electrode surface. The electrode after electrodeposition was rinsed with a lot of ultrapure water, and then subjected to UV irradiation at a wavelength of 300 nm to photo-cross-link the micellar film on the electrode. The electrode was soaked in ethyl acetate solution under stirring for 6 hours to extract the TNT and the target electrode modified with molecularly imprinted micelles electrodeposited film (namely "MIP electrode") was finally obtained. The MIP electrode was connected with electrochemical workstation to form the molecular recognition sensor. The obtained MIP sensor possesses good selectivity for TNT, with the detection limit of $2.0 \times 10^{-8}$ mol/L and the linear response range from $5.0 \times 10^{-6} \sim 5.0 \times 10^{-8}$ mol/L. The sensor shows a little response to 1,3,5-trinitrobenzene and 1,3-dinitrotoluene which are similar to TNT in molecular structure.

Example 7

(1) Preparation of Ionic Photosensitive Copolymer

The synthesis of ionic photosensitive copolymer is the same as example 5.

(2) Preparation of Molecularly Imprinted Polymeric Micelles

The preparation of the molecularly imprinted polymeric micelles entrapping mintacol molecules were the same as example 5. Additionally, hybrids of multiwall carbon nanotubes (MCNTs) and poly(styrene-co-acrylic-2-(dimethylamino)ethyl ester)) (abbreviated as P(St-co-DM)) were prepared and used as conducting materials. The electrolyte for electrodeposition consisted of the molecularly imprinted polymeric micelles and the nanohybrids of MCNTs/P(St-co-DM) in a mass ratio of 9:1.

(3) Preparation of molecular recognition electrochemical sensor: The electrode was treated with "Piranha" solution, rinsed with ultrapure water and ethanol under sonication and dried. The pretreated gold electrode was immersed into the electrolyte and applied with a −10 V potential to make the imprinted micelles as well as nanohybrids move and deposit onto the electrode surface. The electrode after electrodeposition was rinsed with a lot of ultrapure water, and then subjected to UV irradiation at a wavelength of 300 nm to photo-cross-link the micellar film on the electrode. The electrode was subsequently soaked in ethyl acetate solution under stirring for 6 hours to extract the mintacol and obtain the target electrode modified with molecularly imprinted micelles electrodeposited film (namely "MIP electrode"). The MIP electrode was connected with electrochemical workstation to form the molecular recognition sensor. The obtained MIP sensor possesses good selectivity for mintacol, with the detection limit of $2.0 \times 10^{-8}$ mol/L and the linear response range from $5 \times 10^{-3} \sim 8.0 \times 10^{-8}$ mol/L. The sensor shows negligible response to the analogues of mintacol, phoxim, and nitrobenzene. The sensor shows a better performance than that in example 5.

The above examples were used to illustrate the present invention rather than limit the present invention, within the scope of protection in the spirit and claims of the present invention, any amendments and change to the present invention are within the scope of the protection of the present invention.

What is claimed is:

1. A method for preparing a molecular recognition sensor by electrodeposition comprising: (a) forming molecularly imprinted polymeric micelles having one or more template molecules; (b) forming a film on a surface of an electrode by electrodepositing said molecularly imprinted polymeric micelles; (c) crosslinking said molecularly imprinted polymeric micelles of said film; (d) extracting said template molecules from said film to obtain a modified electrode; and (e) incorporating said modified electrode with a sensor device to obtain a molecular recognition sensor.

2. The method of claim 1, wherein said molecular recognition sensor is for specifically detecting the template molecules.

3. The method of claim 2, wherein said molecularly imprinted polymeric micelles is formed by self-assembly of ionic type photosensitive copolymers.

4. The method of claim 2, wherein in step (b) said film is formed at a constant potential.

5. The method of claim 2, wherein in step (c) said molecularly imprinted polymeric micelles in said film is cross-linked via ultraviolet light irradiation.

6. The method of claim 1, wherein said molecularly imprinted polymeric micelles is prepared by (aa) dissolving one or more ionic photosensitive copolymers are dissolved in a solvent to afford a polymer solution; (ab) adding and dissolving said template molecules into said polymer solution; and (ac) dropwise adding water to said polymer solution under stirring to induce microphase separation and self-assembling of said ionic photosensitive copolymer and to form ionic type photosensitive molecularly imprinted micelles with said template molecules entrapped therein.

7. The method of claim 6, wherein step (ac) further comprises a quenching process wherein said polymer solution containing said ionic type photosensitive molecularly imprinted micelles is added dropwise into a volume of water and a solvent removing process wherein said solvent is removed dialysis or evaporation to afford an aqueous solution with 0.1–30% by weight said ionic type photosensitive molecularly imprinted micelles.

8. The method of claim 7, wherein film-formation in step (b) is accomplished by (ba) cleaning said electrode with a solution which is a 1:3 mixture of 30% $H_2O_2$ and conc. sulfuric acid, followed by rising with water and alcohol; (bb) immersing said electrode into said aqueous solution of ionic type photosensitive molecularly imprinted micelles obtained in step (ac); and (bc) applying a constant potential to electrodeposite said micelles onto the surface of said electrode and form a film.

9. The method of claim 8, wherein said crosslinking in step (c) is accomplished by subjecting said electrode covered with a film from step (b) to UV irradiation to lock the structure of said film.

10. The method of claim 9, wherein said crosslinking in step (d) is accomplished by immersing said electrode into a polar solvent under stirring for 1~36 hours to extract said template molecules, followed by rinsing with water.

11. The method of claim 6, wherein said solvent in step (aa) is one solvent or two mixed solvents selected from the group consisting of dimethylformamide, dimethyl sulfoxide, tetrahydrofuran, acetone, isopropyl alcohol, butanol, methanol, 2-butoxyethanol, and acetonitrile.

12. The method of claim 6, wherein said polymer solution in step (aa) is adjusted to pH 2~5 or 8~12 by adding an acid or alkali solution, said acid being hydrochloric acid, acetic acid, formic acid, lactic acid, propionic acid, butyrate, sulfuric acid, methane sulfonic acid, or hydroxyl propane sulfonic acid and said alkali being sodium hydroxide, potassium hydroxide, triethylamine, diethanolamine, triethanolamine or ammonia.

13. The method of claim 10, wherein said polar solvent is one solvent or two mixed solvents selected from the group consisting of water, acetic acid, ethanol, methanol, acetonitrile, N,N-dimethylformamide, dimethyl sulfoxide, and ethyl acetate.

14. The method of claim 1, wherein said template molecule is for food safety testing, selected from the group consisting of antibiotic, hormone, tonyred, melamine, methanal, mintacol, thiophos, nicotine, morphine and caffeine; for bio-pharmaceuticals, selected from the group consisting of glucose, adrenaline, dopamine, ascorbic acid, purine, pyrimidine, DNA, protein and amino acid; or for environmental monitoring, selected from the group consisting of trinitrotoluene, formaldehyde, paraquat and vomitoxin.

15. The method of claim 1, wherein said electrode is of a conductive material, selected from the group consisting of gold, platinum, glassy carbon, stainless steel, tinplate and ITO conductive glass.

16. The method of claim 1, wherein said sensor is capable of outputting signals that are recognizable by computer.

17. The method of claim 1, wherein said template molecules interact with sadi ionic photosensitive copolymer via hydrogen bonding, electrostatic interaction, or coordination.

18. The method of claim 1, wherein in step (b) said film is formed at a constant potential contrary to the charge of said molecularly imprinted micelles, at −30 V to +30 V, for 5 seconds to 10 minutes.

19. The method of claim 1, further comprises a step of adjusting thickness, density, or both thickness and density of said film formed on said electrode in step (b) by varying the concentration of said molecularly imprinted micelles or one or more electrodeposition parameters.

20. The method of claim 1, further comprises a step of adding one or more conducting materials into an electrodepositing electrolyte of said electrodeposition process in step (b), said conducting materials being carbon nanotube, grapheme, gold nanoparticles, or silver nanoparticles, which are modified with amphiphilic copolymers or surfactants.

* * * * *